(12) United States Patent
Kirsch et al.

(10) Patent No.: US 6,551,666 B2
(45) Date of Patent: Apr. 22, 2003

(54) CYCLOHEXANE DERIVATIVES AND LIQUID-CRYSTALLINE MEDIUM

(75) Inventors: Peer Kirsch, Darmstadt (DE); Joachim Krause, Dieburg (DE); Michael Heckmeier, Muehltal (DE)

(73) Assignee: Merck Patent Gesellschaft Mit, Darmstadt (DE)

( * ) Notice: Subject to any disclaimer, the term of this patent is extended or adjusted under 35 U.S.C. 154(b) by 91 days.

(21) Appl. No.: 09/892,775

(22) Filed: Jun. 28, 2001

(65) Prior Publication Data

US 2002/0134967 A1 Sep. 26, 2002

(30) Foreign Application Priority Data

Jun. 28, 2000 (DE) .......................... 100 31 382

(51) Int. Cl.[7] .......................... C09K 19/30; C07C 69/76; C07C 25/18
(52) U.S. Cl. ............ 428/1.1; 252/299.63; 560/65; 570/127; 570/128; 570/130; 570/131
(58) Field of Search ............. 252/299.63, 299.2; 428/1.1; 570/130, 131, 127, 128; 560/65

(56) References Cited

FOREIGN PATENT DOCUMENTS

JP       08311448    * 11/1996

OTHER PUBLICATIONS

English translation for JP 08–311448 by computer http://www6.ipdl.jpo.go.jp/Tokujitu/PAJdetail.ipdl?N0000=60&N0120=01&N2001=2&N3001=H08–311448.*

Tamai et al. "FLC Mixtures Containing Laterally Fluorinated Compounds with an Acetylene Linkage for –Vmin Mode", Bulletin of the CHem. Soci. of Japan, 67(9), 2550–3, 1994.*

* cited by examiner

*Primary Examiner*—Shean C. Wu
(74) *Attorney, Agent, or Firm*—Millen, White, Zelano & Branigan, P.C.

(57) ABSTRACT

The invention relates to cyclohexane derivatives of the formula I

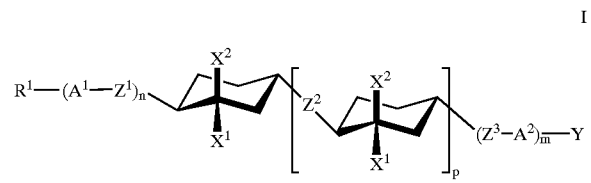

in which n, m, p, $R^1$, $X^1$, $X^2$, $Z^1$, $Z^2$, $Z^3$, $A^1$ $A^2$ and Y are as defined above.

10 Claims, No Drawings

CYCLOHEXANE DERIVATIVES AND LIQUID-CRYSTALLINE MEDIUM

The invention relates to novel cyclohexane derivatives of the formula I

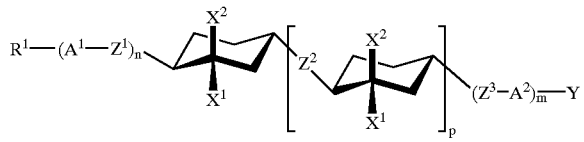

in which
- Y is alkyl or alkoxy having 1 to 10 carbon atoms which is unsubstituted or at least monosubstituted by halogen up to perhalo, is alkenyl or alkenyloxy having 2 to 10 carbon atoms which is unsubstituted or at least monosubstituted by —CN, —CF$_3$ or —F, or is —CN, —F, —OCHF$_2$, —OCF$_3$, —OCHFCF$_3$ or —OCF$_2$CF$_3$,
- one of X$^1$ and
- X$^2$ is CF$_3$, CHF$_2$, CH$_2$F, OCHF$_2$, OCF$_3$, SF$_5$ or an alkyl radical having 2 to 10 carbon atoms which is monosubstituted or polysubstituted by fluorine or chlorine, and one of X$^1$ or X$^2$ in each cyclohexane ring is H,
- R$^1$ is H, an alkyl or alkenyl radical having 1 to 12 carbon atoms which is unsubstituted, monosubstituted by CN or CF$_3$ or at least monosubstituted by halogen, where one or more non-adjacent CH$_2$ groups in these radicals may also, in each case independently of one another, be replaced by

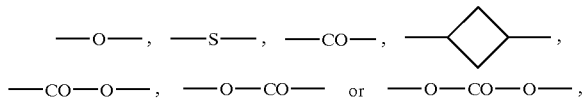

- A$^1$ and A$^2$, independently of one another, are
  a) a trans-1,4-cyclohexylene radical, in which, in addition, one or more, preferably up to two, non-adjacent CH$_2$ groups may be replaced by —O— and/or —S—,
  b) a 1,4-phenylene radical, in which, in addition, one or two CH groups may be replaced by N,
  c) a radical from the group consisting of 1,4-bicyclo [2.2.2]-octylene, piperidine-1,4-diyl, naphthalene-2,6-diyl, deca-hydronaphthalene-2,6-diyl and 1,2,3,4-tetrahydro-naphthalene-2,6-diyl,
  d) 1,4-cyclohexenylene,
  where the radicals a), b) and d) may be substituted by CN, Cl or F, e.g., 0–4 times,
- Z$^1$, Z$^2$ are each, independently of one another, —CO—O—, —O—CO—,
- and Z$^3$—CH$_2$O—, —O—, —O—CH$_2$—, —CH$_2$CH$_2$—, —CH=CH—, —C≡C—, —CF$_2$CF$_2$—CF$_2$O—, —OCF$_2$— or a single bond,
- n and m, independently of one another, are 0, 1, 2 or 3, and
- p is 0, 1, 2 or 3,
- where m+n+p is 1, 2, 3 or 4.

The invention also relates to the use of the compounds of the formula I as components of liquid-crystalline media, and to liquid-crystal and electro-optical display elements which contain the liquid-crystalline media according to the invention.

The compounds of the formula I can be used as components of liquid-crystalline media, in particular for displays based on the principle of the twisted cell, the guest-host effect, the effect of deformation of aligned phases DAP or ECB (electrically controlled birefringence) or the effect of dynamic scattering.

The substances employed hitherto for this purpose all have certain disadvantages, for example inadequate stability to the action of heat, light or electric fields, or unfavorable elastic and/or dielectric properties.

Similar compounds have already been disclosed in DE 19723276. However, this document only relates to compounds having axial F, Cl or CN, which are not covered by the present application. The laterally substituted cyclohexane derivatives covered by DE 3510432 preferably have equatorially arranged substituents. However, the subject-matter of the present application differs through the nature of the substituents.

The invention had the object of finding novel stable liquid-crystalline or mesogenic compounds having negative or low positive dielectric anisotropy which are suitable as components of liquid-crystalline media, in particular for TFT and STN displays.

It has now been found that the compounds of the formula I are eminently suitable as components of liquid-crystalline media. They can be used to obtain stable liquid-crystalline media, in particular suitable for TFT or STN displays. The novel compounds are distinguished, in particular, by high thermal stability, which is advantageous for a high holding ratio, and exhibit favorable clearing point values. Preferred compounds of the formula I have negative dielectric anisotropy and are therefore particularly suitable for displays based on the effect of deformation of aligned phases.

The provision of compounds of the formula I very generally considerably broadens the range of liquid-crystalline substances which are suitable from various applicational points of view for the preparation of liquid-crystalline mixtures.

The compounds of the formula I have a broad range of applications. Depending on the choice of substituents, these compounds may serve as base materials of which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimise its threshold voltage and/or its viscosity. The meaning of the formula I covers all isotopes of the chemical elements bound in the compounds of the formula I. The meaning of the formula I likewise covers both enantiomers of the respective compounds of the formula I. In enantiomerically pure or enriched form, the compounds of the formula I are also suitable as chiral dopants and in general for achieving chiral mesophases. One of ordinary skill can, with routine experimentation, determine the characteristics and properties needed to optimize the compounds and mixtures for use in these and other displays, as is wholly conventional in the art.

In the pure state, the compounds of the formula I are colorless and form liquid-crystalline mesophases in a temperature range which is favourably located for electro-optical use. They are stable chemically, thermally and to light.

The invention thus relates to the compounds of the formula I and to the use of these compounds as components of liquid-crystalline media. The invention furthermore relates to liquid-crystalline media having a content of at least one compound of the formula I and to liquid-crystal display elements, in particular electro-optical display elements, which contain media of this type.

Above and below, n, m, p, $R^1$, $X^1$, $X^2$, $Z^1$, $Z^2$, $Z^3$, $A^1$ $A^2$ and Y are as defined above, unless expressly stated otherwise. If the radical $X^1$ occurs more than once, it may adopt identical or different meanings. The same applies to $X^2$, $A^1$, $A^2$, $Z^1$, $Z^2$ and $Z^3$.

For reasons of simplicity, Cyc below denotes a 1,4-cyclohexylene radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical and Bco denotes a bicyclo[2.2.2]octylene radical, where Cyc and/or Phe may be unsubstituted or monosubstituted or polysubstituted by Cl, F or CN.

W denotes the following structural unit:

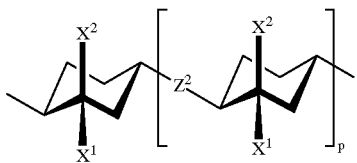

in which p, $X^1$, $X^2$, $X^3$ and $Z^2$ are as defined above.

Formula I thus encompasses, i.a., compounds of the sub-formula Ia:

$R^1$—W—Y    Ia compounds of the sub-formulae Ib, Ic and Id:

$R^1$—W—$A^2$—Y    Ib

R—W—$Z^3$—$A^2$—Y    Ic $R^1$—$A^1$—$Z^1$—W—Y    Id compounds of the sub-formulae Ie to Ii:

$R^1$—W—$A^2$—$A^2$—Y    Ie $R^1$—W—$A^2$—$Z^3$—$A^2$—Y    If $R^1$—W—$Z^3$—$A^2$—$A^2$—Y    Ig $R^1$—W—$Z^3$—$A^2$—$Z^3$—$A^2$—Y    Ih $R^1$—$A^1$—$Z^1$—W—$A^2$—Y    Ii and compounds of the sub-formulae Ij to Ir:

$R^1$—W—$A^2$—$A^2$—$A^2$—Y    Ij $R^1$—W—$Z^3$—$A^2$—$A^2$—$A^2$—Y    Ik $R^1$—W—$A^2$—$Z^3$—$A^2$—$A^2$—Y    Il $R^1$—W—$A^2$—$A^2$—$Z^3$—$A^2$—Y    Im $R^1$—W—$Z^3$—$A^2$—$Z^3$—$A^2$—$A^2$—Y    In $R^1$—W—$Z^3$—$A^2$—$A^2$—$Z^3$—$A^2$—Y    Io $R^1$—W—$A^2$—$Z^3$—$A^2$—$Z^3$—$A^2$—Y    Ip $R^1$—W—$Z^3$—$A^2$—$Z^3$—$A^2$—$Z^3$—$A^2$—Y    Iq $R^1$—$A^1$—$Z^1$—W—$A^2$—$Z^2$—$A^2$—Y    Ir

Of these, particular preference is given to those of the sub-formulae Ia, Ib, Id, Ie, If, Ih, Ii and Ij.

The preferred compounds of the sub-formula Ib include those of the sub-formulae Iba and Ibb:

$R^1$—W-Phe-Y    Iba $R^1$—W-Cyc-Y    Ibb.

The preferred compounds of the sub-formula Ic include those of the sub-formulae Ica and Icb:

$R^1$—W—$Z^3$-Phe-Y    Ica $R^1$—W—$Z^3$-Cyc-Y    Icb.

The preferred compounds of the sub-formula Id include those of the sub-formulae Ida and Idb:

$R^1$-Dio-$Z^1$—W—Y    Ida $R^1$-Cyc-$Z^1$—W—Y    Idb.

The preferred compounds of the sub-formula Ie include those of the sub-formulae Iea to Ieg:

$R^1$—W-Cyc-Cyc-Y    Iea $R^1$—W-Cyc-Phe-Y    Ieb $R^1$—W-Phe-Phe-Y    Iec $R^1$—W-Pyd-Phe-Y    Ied $R^1$—W-Phe-Cyc-Y    Iee $R^1$—W-Dio-Phe-Y    Ief $R^1$—W-Pyr-Phe-Y    Ieg.

Of these, those of the formulae Iea, Ieb, Iec and Iee are particularly preferred.

The preferred compounds of the sub-formulae If include those of the sub-formulae Ifa to Ifg:

$R^1$—W-Cyc-$Z^3$-Cyc-Y    Ifa $R^1$—W-Cyc-$Z^3$-Phe-Y    Ifb $R^1$—W-Phe-$Z^3$-Phe-Y    Ifc $R^1$—W-Pyr-$Z^3$-Phe-Y    Ifd $R^1$—W-Pyd-$Z^3$-Phe-Y    Ife $R^1$—W-Cyc-$CH_2$-$CH_2$-Phe-Y    Iff $R^1$—W—$A^2$—$CH_2CH_2$-Phe-Y    Ifg.

The preferred compounds of the sub-formula Ig include those of the sub-formulae Iga to Igb:

$R^1$—W—$Z^3$-Cyc-Cyc-Y    Iga $R^1$—W—$CH_2CH_2$—$A^2$—$A^2$—Y    Igb $R^1$—W—$Z^3$-Cyc-Phe-Y    Igc $R^1$—W—OCO—$A^2$-Phe-Y    Igd $R^1$—W—$Z^3$-Phe-Phe-Y    Ige $R^1$—W—$Z^3$-Pyr-$A^2$—Y    Igf $R^1$—W—$Z^3$-Pyd-$A^2$—Y    Igg $R^1$—W—$Z^3$-Dio-$A^2$—Y    Igh.

Of these, those of the sub-formulae Iga, Igb, Igc and Ige are particularly preferred.

The preferred compounds of the sub-formula Ih include those of the sub-formulae Iha to Ihe:

R$^1$—W—CH$_2$CH$_2$-Phe-Z$^3$—A$^2$—Y     Iha

R$^1$—W—COO—A$^2$—Z$^3$-Phe-Y     Ihb

R$^1$—W—Z$^3$-Cyc-Z$^3$-Cyc-Y     Ihc

R$^1$—W—Z$^3$-Phe-Z$^3$-Phe-Y     Ihd

R$^1$—W—CH$_2$CH$_2$-Cyc-Z$^3$-Phe-Y     Ihe.

The preferred compounds of the sub-formula Ii include those of the sub-formulae Iia to Iie:

R$^1$—CH$_2$CH$_2$—W-Phe-Y     Iia

R$^1$-Dio-W-Phe-Y     Iib

R$^1$-Phe-W-Cyc-Y     Iic

R$^1$-Cyc-W-Cyc-Y     Iid

R$^1$-Dio-CH$_2$CH$_2$—W-Cyc-Y     Iie.

The preferred compounds of the sub-formulae Ij to Ir include those of the sub-formulae Is to Iz:

R$^1$—W—A$^2$-Cyc-Cyc-Y     Is

R$^1$—W—A$^2$-Cyc-Phe-Y     It

R$^1$—W—A$^2$—CH$_2$CH$_2$—A$^2$-Phe-Y     Iu

R$^1$—W—Z$^3$-Cyc-Z$^3$—A$^2$-Phe-Y     Iv

R$^1$—W-Phe-Phe-Phe-Y     Iw

R$^1$—W-Phe-Z$^3$—A$^2$-Phe-Y     Ix

R$^1$—W—A$^2$-Phe-Z$^3$-Phe-Y     Iy

R$^1$—W—Z$^3$—A$^2$-Cyc-Z$^3$-Phe-Y     Iz.

Y is preferably —CN, F, OCF$_3$, straight-chain alkyl or alkoxy having 1 to 10 carbon atoms, alkenyl or alkenyloxy having 2 to 10 carbon atoms, in particular CN, F, alkyl, alkoxy or alkenyl. Very particularly preference is given to alkyl or alkoxy.

The preferred meaning of X$^1$ and X$^2$ is CF$_3$, CHF$_2$, CH$_2$F, OCHF$_2$ or OCF$_3$, in particular CF$_3$.

In the compounds of the formulae above and below, R$^1$ is preferably straight-chain alkyl having 1 to 10 carbon atoms or alkenyl having 2 to 10 carbon atoms, furthermore preferably alkoxy having 1 to 10 carbon atoms.

A$^1$ is preferably Phe, Cyc, Che, Pyd, Pyr or Dio, in particular Cyc or Dio. The compounds of the formula I preferably contain not more than one of the radicals Bco, Pyd, Pyr, Dio or Dit.

Preference is also given to compounds of the formula I and of all sub-formulae in which Al is 1,4-phenylene which is monosubstituted or disubstituted by F or CN.

A$^1$ is preferably

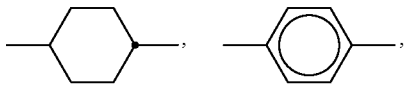

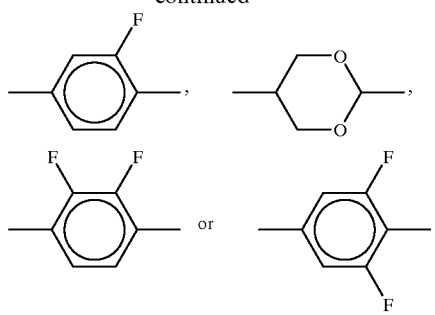

n is preferably 0 or 1, particularly preferably 0. m and p are preferably 0,1 or 2, particularly preferably 0 or 1. Z$^1$, Z$^2$ and Z$^3$ are preferably, independently of one another, —CH$_2$CH$_2$—, —CH=CH— or a single bond, particularly preferably a single bond or —CH$_2$—CH$_2$—.

Preference is given to compounds of the formula I in which R$^1$ and Y are simultaneously alkyl having 1 to 10 carbon atoms, while n is 0 and m is 1.

Particular preference is furthermore given to compounds of the formula I that are characterised in that R$^1$ is straight-chain alkyl or alkoxy having 1 to 10 carbon atoms or alkenyl having 2 to 10 carbon atoms, and Y is alkyl having 1 to 10 carbon atoms, alkenyl having 2 to 10 carbon atoms, —CN, —F, —CHF$_2$ or —OCF$_3$.

Particular preference is given to compounds of the formula I in which X$^1$ or X$^2$ has the same meaning if they occur more than once.

The 1,4-cyclohexenylene group preferably has the following structures:

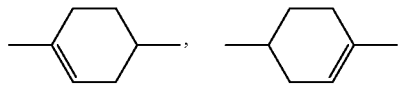

The following group of compounds of the sub-formulae I1 to I15 represents preferred embodiments of the invention:

I1

I2

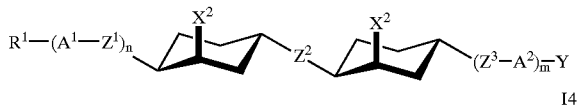

I3

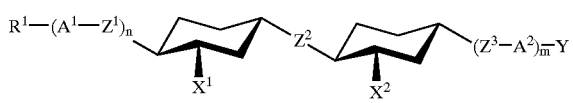

I4

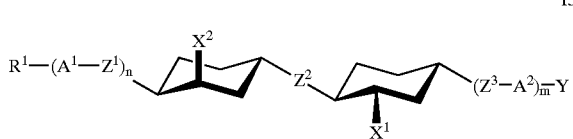

I5

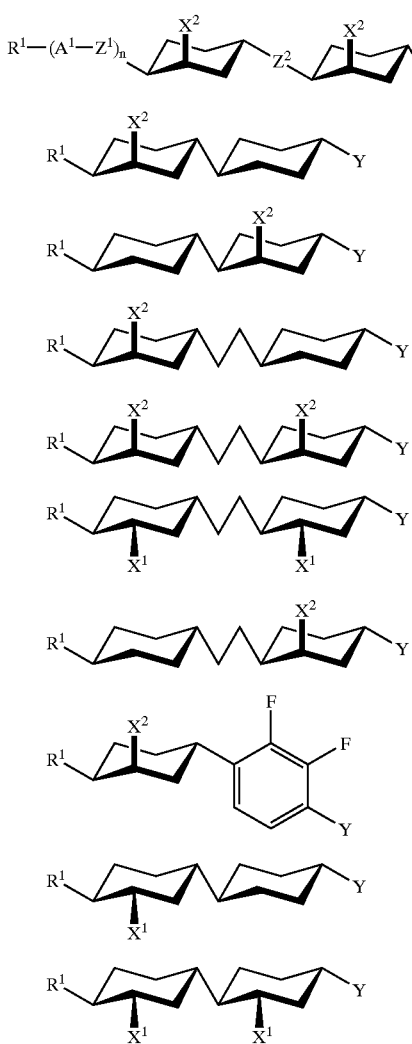
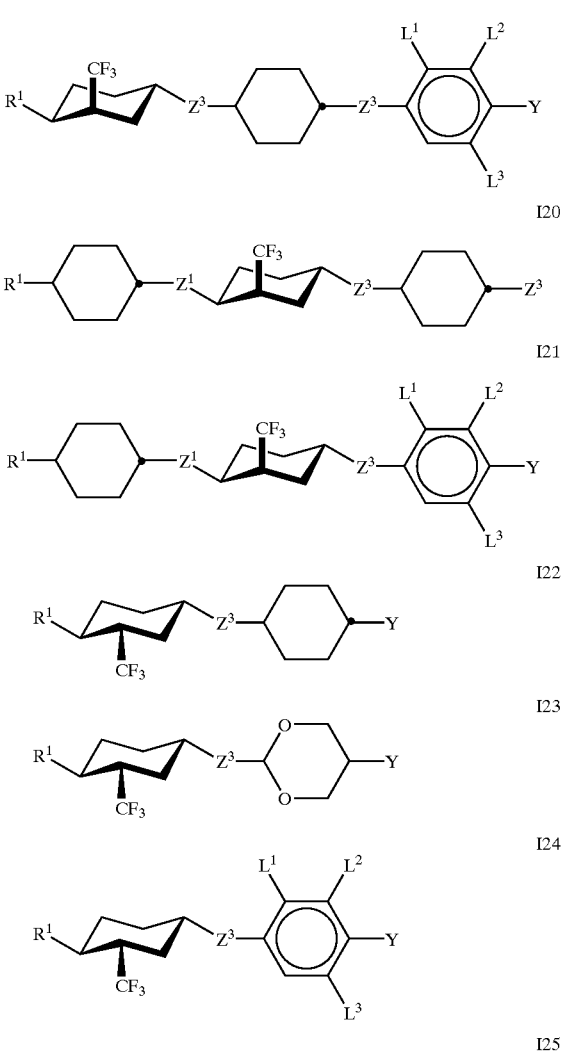
in which n, m, $R^1$, $Z^1$, $Z^2$, $Z^3$, $A^1$, $A^2$ and Y are as defined above. In the formulae I7 to I15, Y is preferably alkyl, alkoxy or oxaalkyl having 1–10 carbon atoms or alkenyl having 2 to 10 carbon atoms.
Particular preference is furthermore given to the compounds of the formulae I16 to I37 from the following group:
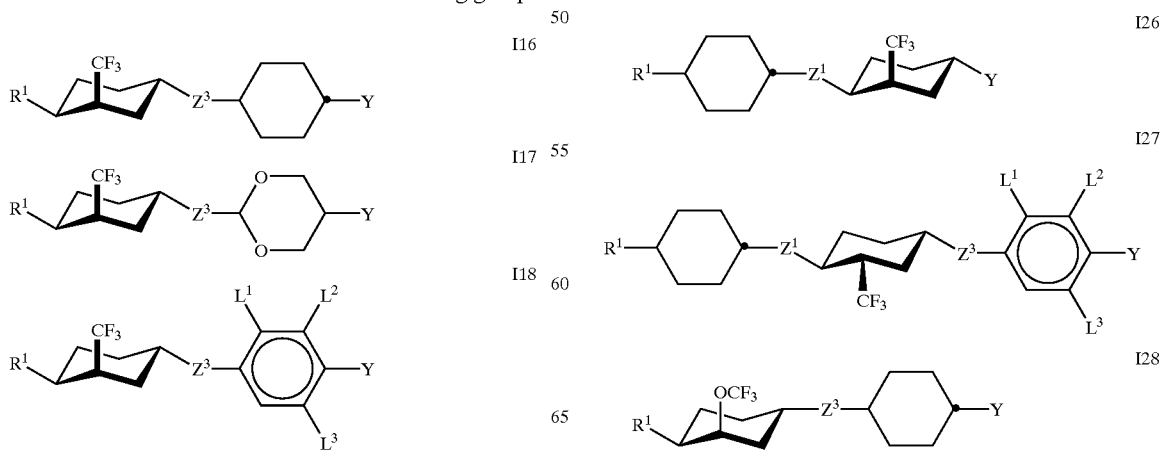

-continued

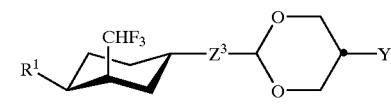
I29

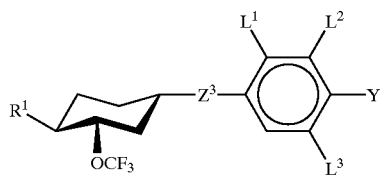
I30

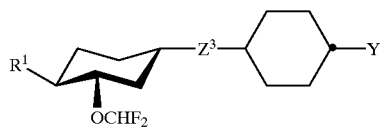
I31

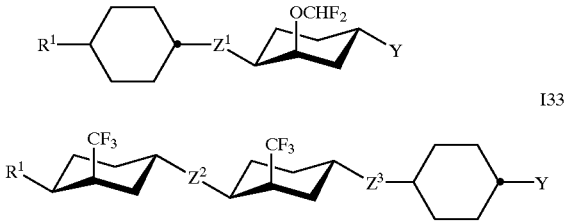
I32

I33

I34

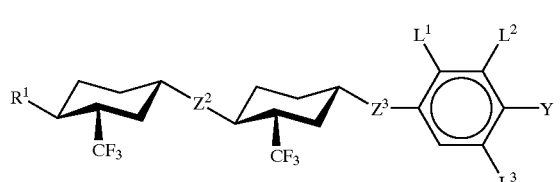
I35

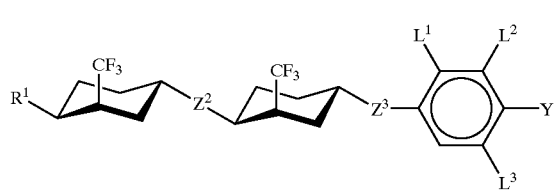
I36

I37 in which $R^1$, $Z^1$, $Z^2$, $Z^3$ and Y are as defined above, $L^1$, $L^2$ and $L^3$ are each, independently of one another, F or H, $L^1$ and $L^2$ preferably being F and $L^3$ preferably being H.

If $R^1$ in the formulae above and below is an alkyl radical and/or an alkoxy radical, this may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexyloxy or heptyloxy, furthermore methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl, e.g., as $R^1$, is preferably straight-chain 2-oxapropyl (=methoxy-methyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ is an alkyl radical in which one $CH_2$ group has been replaced by —CH=CH—, this may be straight-chain or branched. It is preferably straight-chain and has 2 to 10 carbon atoms. Accordingly, it is in particular vinyl, prop-1- or prop-2-enyl, but-1-, -2- or -3-enyl, pent-1-, -2-, -3- or -4-enyl, hex-1-, -2-, -3-, 4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If $R^1$ is an alkyl radical in which one $CH_2$ group has been replaced by —O— and one has been replaced by —CO—, these are preferably adjacent. These thus contain an acyloxy group —CO—O— or an oxycarbonyl group —O—CO. These are preferably straight-chain and have 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If $R^1$ is an alkyl radical in which one $CH_2$ group has been replaced by unsubstituted or substituted —CH=CH— and an adjacent $CH_2$ group has been replaced by CO or CO—O or O—CO, this may be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, 1-methacryoyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If $R^1$ is an alkyl or alkenyl radical which is monosubstituted by CN or $CF_3$, this radical is preferably straight-chain and the substitution by CN or $CF_3$ is in the ω-position.

If $R^1$ is an alkyl or alkenyl radical which is at least monosubstituted by halogen, this radical is preferably straight-chain, and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the ω-position.

Compounds of the formula I having a branched wing group $R^1$ may occasionally be of importance owing to better solubility in the conventional liquid-crystalline base materials, but in particular as chiral dopants if they are optically active. Smectic compounds of this type are suitable as components of ferroelectric materials.

Branched groups of this type generally contain not more than one chain branch. Preferred branched radicals $R^1$ are isopropyl, 2-butyl (=1-methyl-propyl), isobutyl (=2-methylpropyl), 2-methylbutyl, isopentyl (=3-methyl-butyl), 2-methylpentyl, 3-methylpentyl, 2-ethylhexyl, 2-propylpentyl, isopropoxy, 2-methylpropoxy, 2-methylbutoxy, 3-methylbutoxy, 2-methyl-pentoxy, 3-methylpentoxy, 2-ethylhexyloxy, 1-methylhexyloxy and 1-methylheptyloxy.

Formula I covers both the racemates of these compounds and the optical antipodes, and mixtures thereof. Trans isomers are preferred. Resolution, e.g., separation from diastereomeric mixtures, is conventional. See Kirsch and Bremer, Angew. Chem., 112, 2000, 4384 and Handbook of Liquid Crystals (ed. Demus et al., Wiley VCH Weinheim 1998).

Of these compounds of the formula I and the sub-formulae, preference is given to those in which at least one of the radicals present therein has one of the preferred meanings indicated.

In the compounds of the formula I, preference is given to the stereo-isomers in which the rings Cyc and piperidine are trans-1,4-disubstituted. Those of the above-mentioned formulae which contain one or more groups Pyd, Pyr and/or Dio in each case cover the two 2,5-positional isomers.

Some very particularly preferred smaller groups of compounds of the formula I are those of the sub-formulae I38 to I47:

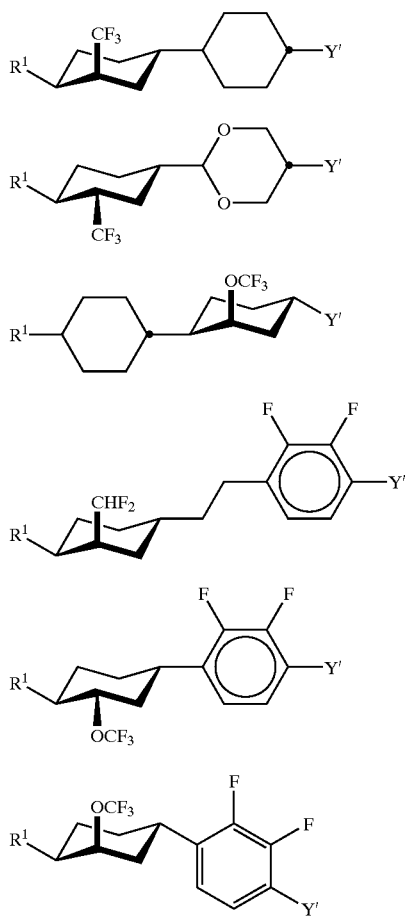

in which $R^1$ is as defined above, and Y' is alkyl, alkoxy, alkenyl or alkenyloxy.

Very particularly preferred compounds from this group are those of the formulae I38, I39, I40, I44 and I45.

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for the said reactions.

Use can also be made here of variants which are known per se, but are not mentioned here in greater detail.

The synthesis of the axially fluorinated compounds of the formula I according to the invention can be achieved by using hydrogen fluoride under pressure or by means of amine/hydrogen fluoride adducts (for example A. V. Grosse, C. B. Linn, J. Org. Chem. 3, (1938) 26; G. A. Olah, M. Nojima, I. Kerekes, Synthesis, (1973) 779); G. A. Olah, X-Y. Li, Q. Wang, G. K. S. Prakash, Synthesis (1993) 693).

The compounds according to the invention can be prepared, for example, in accordance with the following reaction schemes:

Scheme 1

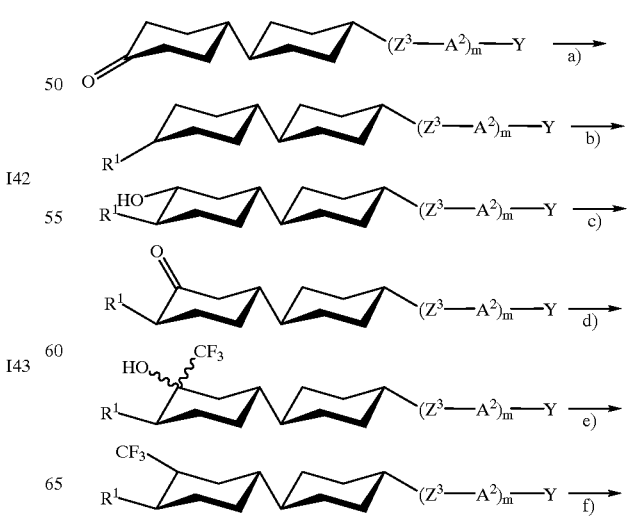

-continued

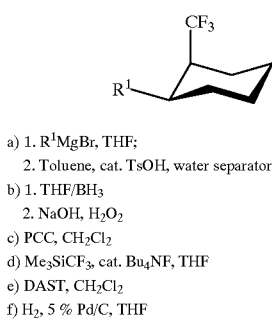

a) 1. R¹MgBr, THF;
   2. Toluene, cat. TsOH, water separator
b) 1. THF/BH₃
   2. NaOH, H₂O₂
c) PCC, CH₂Cl₂
d) Me₃SiCF₃, cat. Bu₄NF, THF
e) DAST, CH₂Cl₂
f) H₂, 5 % Pd/C, THF Scheme 2

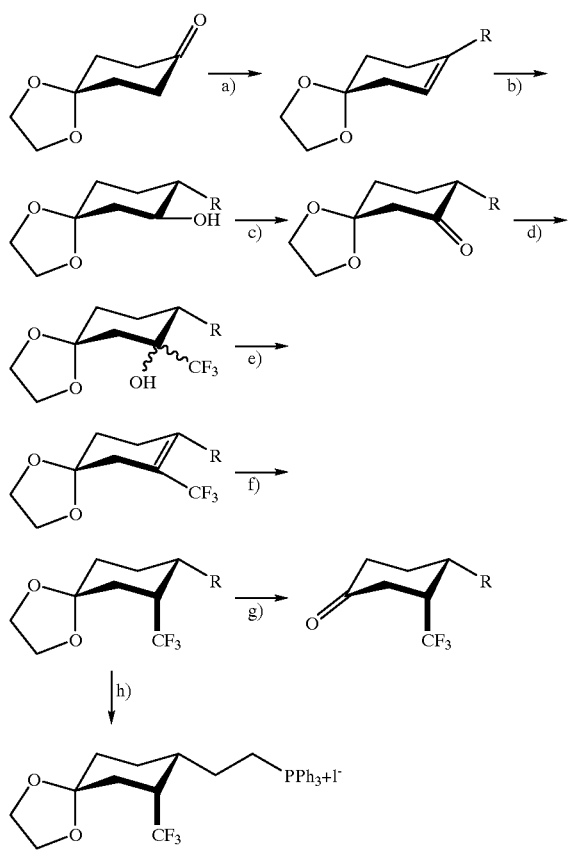

a) 1. RMgBr, THF
   2. Toluene, cat. TsOH, water separator
b) 1. THF/BH₃
   2. NaOH, H₂O₂
c) PCC, CH₂Cl₂
d) Me₃SiCF₃, cat. Bu₄NF, THF
e) DAST, CH₂Cl₂
f) H₂, 5 % Pd/C, THF
g) 98 % HCOOH, toluene
h) R = CH₂CH₂OBn
   1. H₂, Pd-C, THF
   2. MsCl, CH₂Cl₂, NEt₃
   3. KI, acetone
   4. PPh₃, acetonitrile Scheme 3

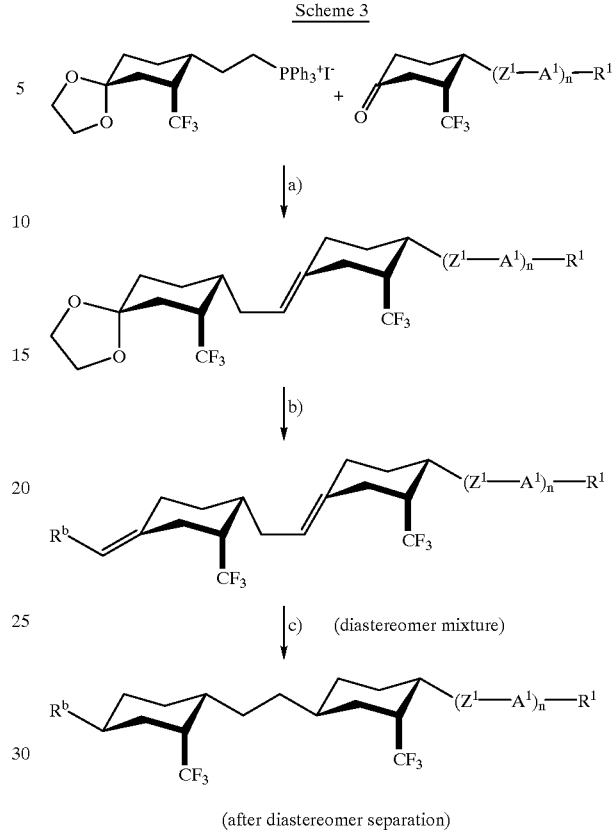

(diastereomer mixture)

(after diastereomer separation)

R$^b$: alkyl a) KOtBu, THF
b) 1. Cat. CBr₄/PPh₃, acetone
   2. R$^b$CH₂PPh₃⁺Br⁻, KOtBu, THF
c) H₂, Pd/C, THF (R¹ = R'CH₂)

Scheme 4

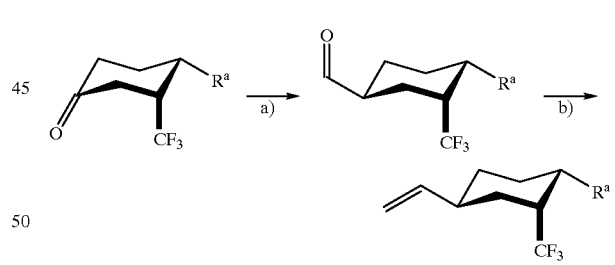

a) 1. CH₃OCH₂PPh₃⁺Br⁻, KOtBu, THF
   2. H⁺/H₂O
b) CH₃PPh₃⁺Br⁻, KOtBu, THF

R$^a$: mesogenic radical

Esters of the formula I can also be obtained by esterification of corresponding carboxylic acids (or their reactive derivatives) using alcohols or phenols (or their reactive derivatives) or by the DCC method (DCC= dicyclohexylcarbodiimide).

The corresponding carboxylic acids and alcohols or phenols are known or can be prepared analogously to known processes.

Nitriles can be obtained by exchange of halogens with copper cyanide or alkali metal cyanide.

In a further process for the preparation of the compounds of the formula I in which $Z^1$, $Z^2$ or $Z^3$ is —CH=CH—, an aryl halide is reacted with an olefin in the presence of a tertiary amine and in the presence of a palladium catalyst (cf. R. F. Heck, Acc. Chem. Res. 12 (1979) 146). Examples of suitable aryl halides are chlorides, bromides and iodides, in particular bromides and iodides. The tertiary amines necessary for the success of the coupling reaction, such as, for example, triethylamine, are also suitable as solvent. Examples of suitable palladium catalysts are the salts thereof, in particular Pd(II) acetate, with organic phosphorus (III) compounds, such as, for example, triarylphosphines. The process can be carried out in the presence or absence of an inert solvent at temperatures between about 0° C. and 150° C., preferably between 20° C. and 100° C.; suitable solvents are, for example, nitriles, such as acetonitrile, or hydrocarbons, such as benzene or toluene. The aryl halides and olefins employed as starting materials are in many cases commercially available or can be prepared by processes known from the literature, for example by halogenation of corresponding parent compounds or by elimination reactions on corresponding alcohols or halides.

In this way, stilbene derivatives, for example, can be prepared. The stilbenes can furthermore be prepared by reaction of a 4-substituted benzaldehyde with a corresponding phosphorus ylide by the Wittig method. However, tolans of the formula I can also be prepared by employing monosubstitued acetylene instead of the olefin (Synthesis 627 (1980) or Tetrahedron Lett. 27, 1171(1986)).

For the coupling of aromatic compounds, it is furthermore possible to react aryl halides with aryltin compounds. These reactions are preferably carried out with addition of a catalyst, such as, for example, a palladium(0) complex, in inert solvents, such as hydrocarbons, at high temperatures, for example in boiling xylene, under a protective gas.

Coupling reactions of alkynyl compounds with aryl halides can be carried out analogously to the process described by A. O. King, E. Negishi, F. J. Villani and A. Silveira in J. Org. Chem 43, 358 (1978).

Tolans of the formula I in which $Z^1$ or $Z^2$ is —C≡C— can also be prepared by the Fritsch-Buttenberg-Wiechell rearrangement (Ann. 279, 319, 1984), in which 1,1-diaryl-2-haloethylenes are rearranged to give diarylacetylenes in the presence of strong bases.

Tolans of the formula I can also be prepared by brominating the corresponding stilbenes, followed by dehydrohalogenation. Use can be made here of variants of this reaction which are known per se, but are not mentioned here in greater detail.

Ethers of the formula I are obtainable by etherification of corresponding hydroxyl compounds, preferably corresponding phenols, where the hydroxyl compound is advantageously firstly converted into a corresponding metal derivative, for example into the corresponding alkali metal alkoxide or alkali metal phenoxide by treatment with NaH, $NaNH_2$, NaOH, KOH, $Na_2CO_3$ or $K_2CO_3$. This metal derivative can then be reacted with the appropriate alkyl halide, alkyl sulfonate or dialkyl sulfate, advantageously in an inert solvent, such as, for example, acetone, 1,2-dimethoxyethane, DMF or dimethyl sulfoxide, or alternatively with an excess of aqueous or aqueous-alcoholic NaOH or KOH, at temperatures between about 20° C. and 100° C.

The starting materials are either known or can be prepared analogously to known compounds.

The compounds of the formula I can be obtained in enantiomerically pure form by conventional methods, preferably by chiral preparative HPLC.

The liquid-crystalline media according to the invention preferably comprise from 2 to 40, in particular from 4 to 30, components as further constituents besides one or more compounds according to the invention. These media very particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterised by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH$_2$CH$_2$—E—R" | 4 |
| R'—L—C≡C—E—R" | 5 |

In the formulae 1, 2, 3, 4 and 5, L and E, which may be identical or different, are each, independently of one another, a divalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl, and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" are each, independently of one another, alkyl, alkenyl, alkoxy, alkoxyalkyl, alkenyloxy or alkanoyloxy having up to 8 carbon atoms. This smaller sub-group is called group A below, and the compounds are referred to by the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5, which is known as group B, R" is —F, —Cl, —NCS or —(O)$_i$CH$_{3-(k+l)}$F$_k$Cl$_l$, where i is 0 or 1, and k and l are 1, 2 or 3; the compounds in which R" has this meaning are referred to by the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is referred to below as group C, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

Besides the preferred compounds of groups A, B and C, other compounds of the formulae 1, 2, 3, 4 and 5 having other variants of the proposed substituents are also customary. All these substances are obtainable by methods which are known from the literature or analogously thereto.

Besides the compounds of the formula I according to the invention, the media according to the invention preferably comprise one or more compounds selected from group A and/or group B and/or group C. The proportions by weight of the compounds from these groups in the media according to the invention are preferably group A: from 0 to 90%, preferably from 20 to 90%, in particular from 30 to 90% group B: from 0 to 80%, preferably from 10 to 80%, in particular from 10 to 65% group C: from 0 to 80%, preferably from 5 to 80%, in particular from 5 to 50%, the sum of the proportions by weight of the group A and/or B and/or C compounds present in the respective media according to the invention preferably being 5%–90% and in particular from 10% to 90%.

The media according to the invention preferably comprise from 1 to 40%, particularly preferably from 5 to 30%, of the compounds according to the invention. Preference is furthermore given to media comprising more than 40%, in particular from 45 to 90%, of compounds according to the invention. The media preferably comprise three, four or five compounds according to the invention.

The media according to the invention are prepared in a manner which is conventional per se. In general, the components are dissolved in one another, advantageously at elevated temperature. By means of suitable additives, the liquid-crystalline phases according to the invention can be modified in such a way that they can be used in all types of liquid-crystal display elements that have been disclosed hitherto. Additives of this type are known to the person skilled in the art and are described in detail in the literature (H. Kelker/R. Hatz, Handbook of Liquid Crystals, Verlag Chemie, Weinheim, 1980). For example, pleochroic dyes can be added for the preparation of colored guest-host systems or substances can be added to modify the dielectric anisotropy, the viscosity and/or alignment of the nematic phases.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above, and of corresponding German application No. DE 100 313 82.5, filed Jun. 28, 2000, is hereby incorporated by reference.

m.p. denotes melting point, cl.p.=clearing point. Furthermore, C=crystalline state, N=nematic phase, Sm=smectic phase and I=isotropic phase. The data between these symbols represent the transition temperatures. Δn denotes optical anisotropy (589 nm, 20 C.) and Δε denotes the dielectric anisotropy (1 kHz, 20° C.). The viscosity (mm$^2$/sec) was determined at 20° C.

"Conventional work-up" means that water is added if necessary, the mixture is extracted with methylene chloride, diethyl ether or toluene, the phases are separated, the organic phase is dried and evaporated, and the product is purified by distillation under reduced pressure or crystallization and/or chromatography.

The following abbreviations are used:

| | |
|---|---|
| PCC | pyridinium chlorochromate |
| THF | tetrahydrofuran |
| KOtBu | potassium tert-butoxide |
| RT | room temperature |
| MTB ether | methyl tert-butyl ether |
| DAST | dimethylaminosulfur trifluoride |

EXAMPLES

Example 1

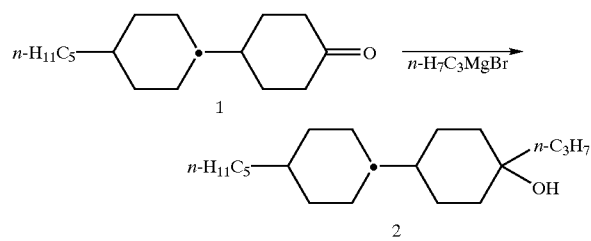

10% of a solution of 80 ml of bromopropane in 200 ml of THF were added dropwise at 60° C. to 21.9 g of magnesium turnings and 200 ml of THF. After the reaction had commenced, the remainder of the solution was added dropwise over the course of 30 minutes under reflux. After the mixture had been stirred at 70 C. for 1 hour, a solution of 200.0 g of 1 in 400 ml of THF was added dropwise. After 30 minutes, the mixture was subjected to conventional work-up, giving 2.

Example 2

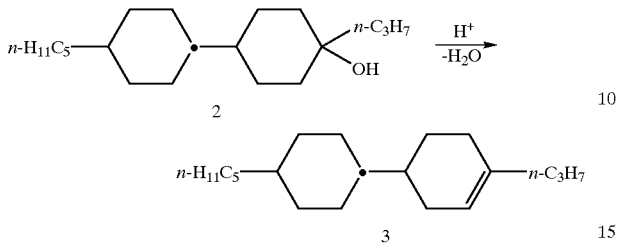

236.0 g of 2,5 ml of 98% sulfuric acid and 1.5 l of toluene were refluxed on a water separator for 1.5 hours. The mixture was cooled to RT and subjected to conventional work-up, giving 3.

Example 3

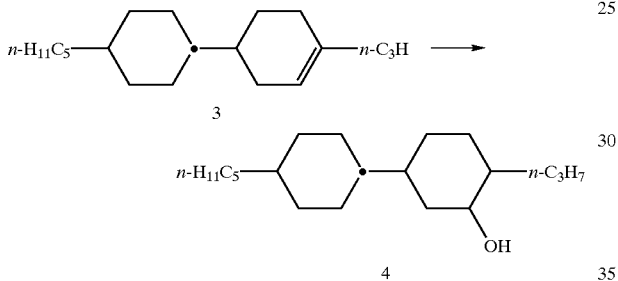

550.0 ml of a 1 M solution of a borane/THF complex in THF were added dropwise with stirring to a solution, cooled to +2° C., of 122.0 g of 3 in 1.0 l of THF. After the mixture had been stirred at +2° C. for 1 hour and at RT for 1 hour, firstly 130 ml of ethanol, then a solution of 28.0 g of sodium hydroxide in water and finally 170 ml of a 30% solution of hydrogen peroxide in water were added dropwise. The mixture was refluxed for 2 hours with stirring, cooled to RT and subjected to conventional work-up, giving 4.

Example 4

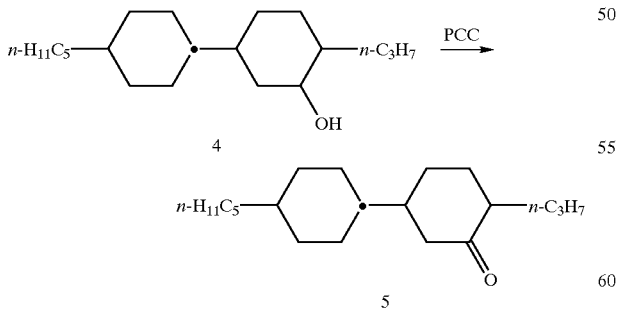

8.62 g of pyridinium chlorochromate were added under nitrogen to a solution of 11.0 g of 4 in 150 ml of dichloromethane. The mixture was stirred overnight and subjected to conventional work-up, giving 5.

Example 5

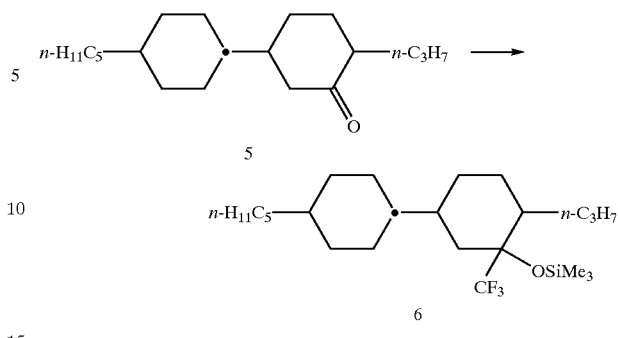

102.4 g of 5 and 1.5 ml of a 26% solution of tetrabutylammonium fluoride in THF were dissolved in 600 ml of THF and cooled to 0° C. 57.65 ml of trifluoromethyltrimethylsilane were subsequently added without exceeding 30 C., and the mixture was stirred at RT for 2 hours. Conventional work-up gave 6.

Example 6

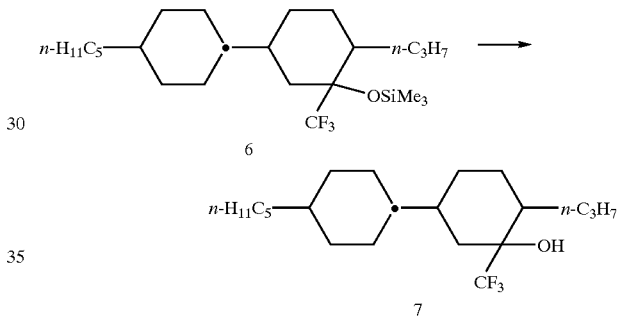

21.5 g of potassium fluoride were added to a solution of 146.1 g of 6 in 500 ml of methanol. After the mixture had been refluxed for 3 hours, the majority of the methanol was distilled off, and 1.0 l of water was added to the residue. Subsequent conventional work-up gave 7.

Example 7

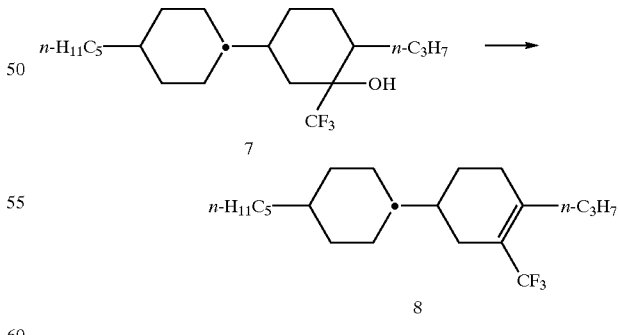

49.6 ml of thionyl chloride were added dropwise with stirring to a solution, cooled to 5° C., of 121.0 g of 7 in 270 ml of pyridine. After the mixture had been stirred for 3 days, the majority of the pyridine and thionyl chloride was distilled off under reduced pressure, and the residue was subjected to conventional work-up, giving 8.

Example 8

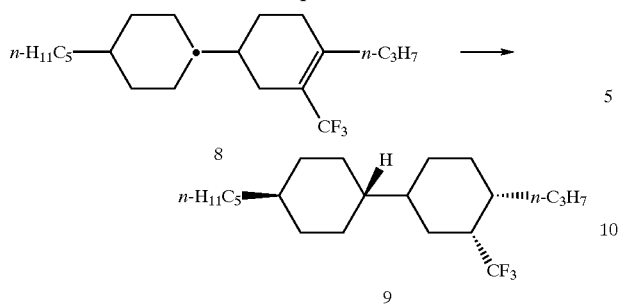

64.4 g of 8 were dissolved in 500 ml of THF and hydrogenated in the presence of 10.0 g of Pd/C (5%). Subsequent conventional work-up and crystallization at −25° C. gave 9.

The following compounds according to the invention are obtained analogously from the corresponding precursors:

Examples 9–23

| | $R^1$ | $Z^3$ | $A^2$ | Y |
|---|---|---|---|---|
| (9) | n-Propyl | — | cyclohexyl | n-Propyl |
| (10) | n-Propyl | —CH$_2$—CH$_2$— | cyclohexyl | n-Pentyl |
| (11) | n-Pentyl | — | cyclohexyl | n-Propyl |
| (12) | n-Pentyl | —CH$_2$—CH$_2$— | cyclohexyl | n-Pentyl |
| (13) | n-Pentyl | — | cyclohexyl | n-Butyl |
| (14) | n-Pentyl | — | cyclohexyl | O-n-Propyl |
| (15) | n-Pentyl | — | cyclohexyl | CH=CH$_2$ |
| (16) | n-Propyl | — | cyclohexyl | trans-(CH$_2$)$_2$CH=CHCH$_3$ |
| (17) | n-Propyl | — | phenyl | CH=CH$_2$ |

-continued
| | R¹ | Z³ | A² | Y |
|---|---|---|---|---|
| (18) | n-Propyl | — | 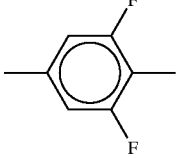 | F |
| (19) | n-Pentyl | — | 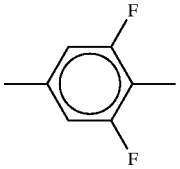 | CN |
| (20) | n-Propyl | —CH₂—CH₂— | 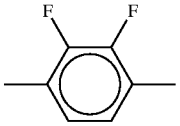 | OCF₃ |
| (21) | n-Pentyl | —COO— |  | CN |
| (22) | n-Pentyl | —CH₂—CH₂— | 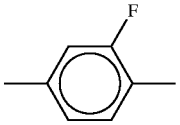 | F |
| (23) | n-Propyl | —CH₂—CH₂— |  | O-n-Propyl |
Examples 24–38
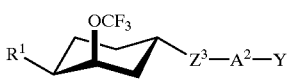
| | R¹ | Z³ | A² | Y |
|---|---|---|---|---|
| (24) | n-Propyl | — | 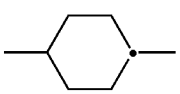 | n-Propyl |
| (25) | n-Propyl | —CH₂CH₂— |  | n-Pentyl |
| (26) | n-Pentyl | — | 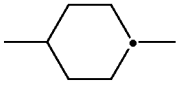 | n-Propyl |

-continued
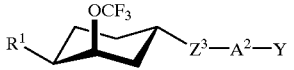
| | R¹ | Z³ | A² | Y |
|---|---|---|---|---|
| (27) | n-Pentyl | —CH₂CH₂— |  | n-Pentyl |
| (28) | n-Pentyl | — | 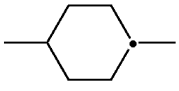 | n-Butyl |
| (29) | n-Pentyl | — | 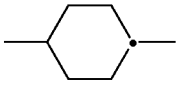 | O-n-Propyl |
| (30) | n-Pentyl | — | 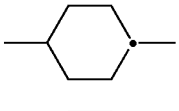 | CH=CH₂ |
| (31) | n-Propyl | — | 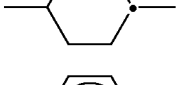 | trans-(CH₂)₂CH=CHCH₃ |
| (32) | n-Propyl | — |  | CH=CH₂ |
| (33) | n-Propyl | — | 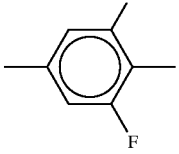 | F |
| (34) | n-Pentyl | — | 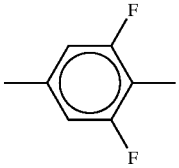 | CN |
| (35) | n-Propyl | —CH₂—CH₂— | 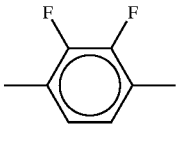 | OCF₃ |
| (36) | n-Pentyl | —COO— |  | CN |
| (37) | n-Pentyl | —CH₂CH₂— | 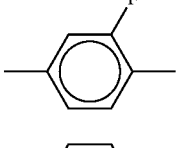 | F |
| (38) | n-Propyl | —CH₂—CH₂— |  | O-n-Propyl |

Examples 39–48

| | R¹ | Z³ | A² | Y |
|---|---|---|---|---|
| (39) | n-Pentyl | — | cyclohexyl | n-Propyl |
| (40) | n-Pentyl | —CH₂—CH₂— | cyclohexyl | n-Pentyl |
| (41) | n-Pentyl | — | cyclohexyl | O-n-Propyl |
| (42) | n-Pentyl | — | cyclohexyl | CH=CH₂ |
| (43) | n-Propyl | — | cyclohexyl | trans-(CH₂)₂CH=CHCH₃ |
| (44) | n-Propyl | — | phenyl | CH=CH₂ |
| (45) | n-Propyl | — | 2,3-difluorophenyl | F |
| (46) | n-Pentyl | — | 2,3-difluorophenyl | CN |
| (47) | n-Propyl | —CH₂—CH₂— | 2,3-difluorophenyl | OCF₃ |
| (48) | n-Propyl | —CH₂—CH₂— | phenyl | O-n-Propyl | where the core structure is: R¹—(cyclohexyl with CF₃ substituent)—Z³—A²—Y

Examples 49–58
| | R¹ | Z³ | A² | Y |
|---|---|---|---|---|
| (49) | n-Pentyl | — | cyclohexyl | n-Propyl |
| (50) | n-Pentyl | —CH₂—CH₂— | cyclohexyl | n-Pentyl |
| (51) | n-Pentyl | — | cyclohexyl | O-n-Propyl |
| (52) | n-Pentyl | — | cyclohexyl | CH=CH₂ |
| (53) | n-Propyl | — | cyclohexyl | trans-(CH₂)₂CH=CHCH₃ |
| (54) | n-Propyl | — | phenyl | CH=CH₂ |
| (55) | n-Propyl | — | 2,3-difluorophenyl | F |
| (56) | n-Pentyl | — | 2,3-difluorophenyl | CN |
| (57) | n-Propyl | —CH₂—CH₂— | 2,3-difluorophenyl | OCF₃ |
| (58) | n-Propyl | —CH₂—CH₂— | phenyl | O-n-Propyl |

Examples 59–68
| | R¹ | Z³ | A² | Y |
|---|---|---|---|---|
| (59) | n-Pentyl | — | 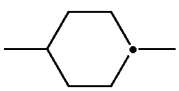 | n-Propyl |
| (60) | n-Pentyl | —CH₂—CH₂— | 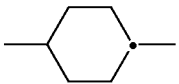 | n-Pentyl |
| (61) | n-Pentyl | — | 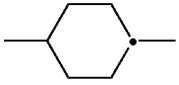 | O-n-Propyl |
| (62) | n-Pentyl | — |  | CH=CH₂ |
| (63) | n-Propyl | — | 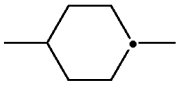 | trans-(CH₂)₂CH=CHCH₃ |
| (64) | n-Propyl | — |  | CH=CH₂ |
| (65) | n-Propyl | — | 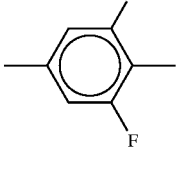 | F |
| (66) | n-Pentyl | — | 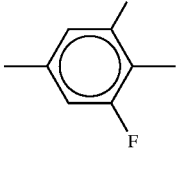 | CN |
| (67) | n-Propyl | —CH₂—CH₂— | 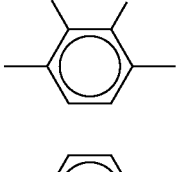 | OCF₃ |
| (68) | n-Propyl | —CH₂—CH₂— |  | O-n-Propyl |

Examples 69–78
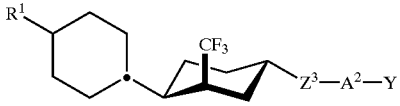
| | R¹ | Z³ | A² | Y |
|---|---|---|---|---|
| (69) | n-Pentyl | — |  | n-Propyl |
| (70) | n-Pentyl | —CH₂—CH₂— |  | n-Pentyl |
| (71) | n-Pentyl | — |  | O-n-Propyl |
| (72) | n-Pentyl | — |  | CH=CH₂ |
| (73) | n-Propyl | — |  | trans-(CH₂)₂CH=CHCH₃ |
| (74) | n-Propyl | — |  | CH=CH₂ |
| (75) | n-Propyl | —CO—O— |  | F |
| (76) | n-Pentyl | — |  | CN |
| (77) | n-Propyl | —CH₂—CH₂— |  | OCF₃ |
| (78) | n-Propyl | —CH₂—CH₂— |  | O-n-Propyl |

Examples 79–88
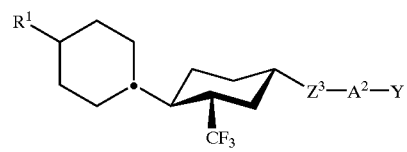
| | R¹ | Z³ | A² | Y |
|---|---|---|---|---|
| (79) | n-Pentyl | — | cyclohexyl | n-Propyl |
| (80) | n-Pentyl | —CH₂—CH₂— | cyclohexyl | n-Pentyl |
| (81) | n-Pentyl | — | cyclohexyl | O-n-Propyl |
| (82) | n-Pentyl | — | cyclohexyl | CH=CH₂ |
| (83) | n-Propyl | — | cyclohexyl | trans-(CH₂)₂CH=CHCH₃ |
| (84) | n-Propyl | —CO—O— | phenyl | CH=CH₂ |
| (85) | n-Propyl | — | 2,3-difluorophenyl | F |
| (86) | n-Pentyl | — | 2,3-difluorophenyl | F |
| (87) | n-Propyl | —CH₂—CH₂— | 2,3-difluorophenyl | OCF₃ |
| (88) | n-Propyl | —CH₂—CH₂— | phenyl | O-n-Propyl |

Examples 89–98
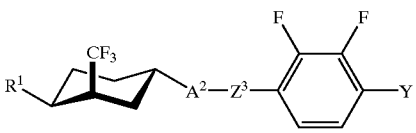
| | R¹ | Z³ | A² | Y |
|---|---|---|---|---|
| (89) | n-Pentyl | — | 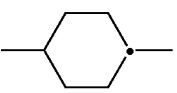 | n-Propyl |
| (90) | n-Pentyl | —CH₂—CH₂— | 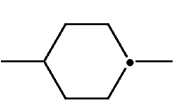 | n-Pentyl |
| (91) | n-Pentyl | — | 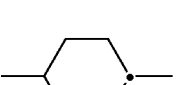 | O-n-Propyl |
| (92) | n-Pentyl | — | 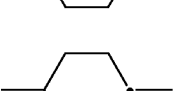 | CH=CH₂ |
| (93) | n-Propyl | — | 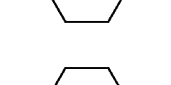 | trans-(CH₂)₂CH=CHCH₃ |
| (94) | n-Propyl | —CO—O— |  | CH=CH₂ |
| (95) | n-Propyl | — | 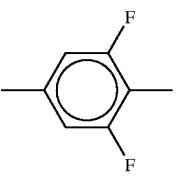 | F |
| (96) | n-Pentyl | — | 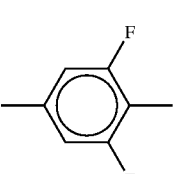 | CN |
| (97) | n-Propyl | —CH₂—CH₂— | 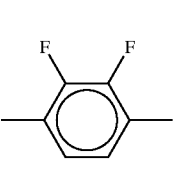 | OCF₃ |
| (98) | n-Propyl | —CH₂—CH₂— |  | O-n-Propyl |

Examples 99–108
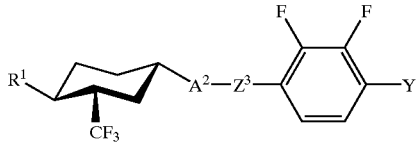
| | R¹ | Z³ | A² | Y |
|---|---|---|---|---|
| (99) | n-Pentyl | — | 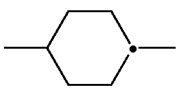 | n-Propyl |
| (100) | n-Pentyl | —CH₂—CH₂— |  | n-Pentyl |
| (101) | n-Pentyl | — |  | O-n-Propyl |
| (102) | n-Pentyl | — | 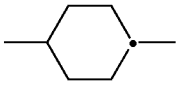 | CH=CH₂ |
| (103) | n-Propyl | — | 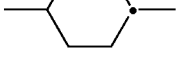 | trans-(CH₂)₂CH=CHCH₃ |
| (104) | n-Propyl | —CO—O— |  | CH=CH₂ |
| (105) | n-Propyl | — | 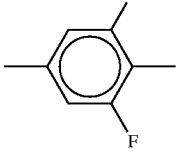 | F |
| (106) | n-Pentyl | — | 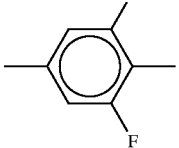 | CN |
| (107) | n-Propyl | —CH₂—CH₂— | 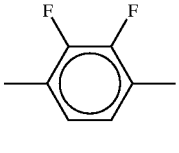 | OCF₃ |
| (108) | n-Propyl | —CH₂—CH₂— |  | O-n-Propyl |

Examples 109–118
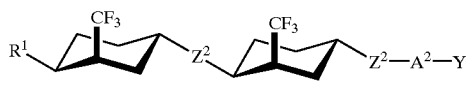
| | R¹ | Z² | Z³ | A² | Y |
|---|---|---|---|---|---|
| (109) | n-Pentyl | — | — | — | n-Propyl |
| (110) | n-Pentyl | —CH₂—CH₂— | — | — | n-Pentyl |
| (111) | n-Pentyl | — | — | 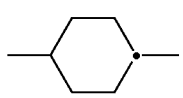 | O-n-Propyl |
| (112)n | n-Pentyl | — | — | 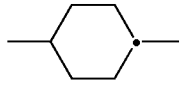 | CH=CH₂ |
| (113) | n-Propyl | —CH₂—CH₂— | — | 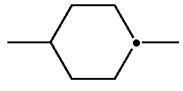 | trans-(CH₂)₂CH=CHCH₃ |
| (114) | n-Propyl | —CH₂—CH₂— | — |  | CH=CH₂ |
| (115) | n-Propyl | — | — | 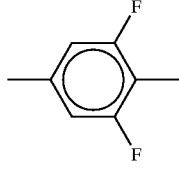 | F |
| (116) | n-Pentyl | — | — | 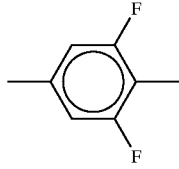 | CN |
| (117) | n-Propyl | — | —CH₂—CH₂— | 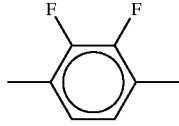 | OCF₃ |
| (118) | n-Propyl | — | —CH₂—CH₂— |  | O-n-Propyl |
Examples 119–128
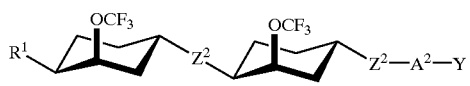
| | R¹ | Z² | Z³ | A² | Y |
|---|---|---|---|---|---|
| (119) | n-Pentyl | — | — | — | n-Propyl |
| (120) | n-Pentyl | —CH₂—CH₂— | — | — | n-Pentyl |

-continued

*Structure: R¹—[cyclohexane with OCF₃]—Z²—[cyclohexane with OCF₃]—Z³—A²—Y*

| | R¹ | Z² | Z³ | A² | Y |
|---|---|---|---|---|---|
| (121) | n-Pentyl | — | — | [cyclohexyl] | O-n-Propyl |
| (122)n | n-Pentyl | — | — | [cyclohexyl] | CH=CH₂ |
| (123) | n-Propyl | —CH₂—CH₂— | — | [cyclohexyl] | trans-(CH₂)₂CH=CHCH₃ |
| (124) | n-Propyl | —CH₂—CH₂— | — | [phenyl] | CH=CH₂ |
| (125) | n-Propyl | — | — | [2,3-difluorophenyl] | F |
| (126) | n-Pentyl | — | — | [2,3-difluorophenyl] | CN |
| (127) | n-Propyl | — | —CH₂—CH₂— | [2,3-difluorophenyl] | OCF₃ |
| (128) | n-Propyl | — | —CH₂—CH₂— | [phenyl] | O-n-Propyl |

Examples 129–138

*Structure: R¹—[cyclohexane with CF₃]—Z²—[cyclohexane with CF₃]—Z³—A²—Y*

| | R¹ | Z² | Z³ | A² | Y |
|---|---|---|---|---|---|
| (129) | n-Pentyl | — | — | — | n-Propyl |
| (130) | n-Pentyl | —CH₂—CH₂— | — | — | n-Pentyl |
| (131) | n-Pentyl | — | — | [cyclohexyl] | O-n-Propyl |

-continued

R¹–[cyclohexyl(CF₃)]–Z²–[cyclohexyl(CF₃)]–Z²–A²–Y

| | R¹ | Z² | Z³ | A² | Y |
|---|---|---|---|---|---|
| (132)n | n-Pentyl | — | — | cyclohexyl | CH=CH₂ |
| (133) | n-Propyl | —CH₂—CH₂— | — | cyclohexyl | trans-(CH₂)₂CH=CHCH₃ |
| (134) | n-Propyl | —CH₂—CH₂— | — | phenyl | CH=CH₂ |
| (135) | n-Propyl | — | — | 2,3-difluorophenyl | F |
| (136) | n-Pentyl | — | — | 2,3-difluorophenyl | CN |
| (137) | n-Propyl | — | —CH₂—CH₂— | 2,3-difluorophenyl | OCF₃ |
| (138) | n-Propyl | — | —CH₂—CH₂— | phenyl | O-n-Propyl |

Examples 139–148

R¹–[cyclohexyl(OCF₃)]–Z²–[cyclohexyl(OCF₃)]–Z²–A²–Y

| | R¹ | Z² | Z³ | A² | Y |
|---|---|---|---|---|---|
| (139) | n-Pentyl | — | — | — | n-Propyl |
| (140) | n-Pentyl | —CH₂—CH₂— | — | — | n-Pentyl |
| (141) | n-Pentyl | — | — | cyclohexyl | O-n-Propyl |

-continued

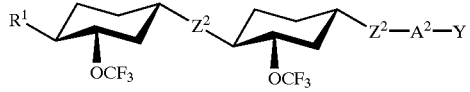

| | R¹ | Z² | Z³ | A² | Y |
|---|---|---|---|---|---|
| (142)n | n-Pentyl | — | — | (cyclohexyl) | CH=CH$_2$ |
| (143) | n-Propyl | —CH$_2$—CH$_2$— | — | (cyclohexyl) | trans-(CH$_2$)$_2$CH=CHCH$_3$ |
| (144) | n-Propyl | —CH$_2$—CH$_2$— | — | (phenyl) | CH=CH$_2$ |
| (145) | n-Propyl | — | — | (3,5-difluorophenyl) | F |
| (146) | n-Pentyl | — | — | (3,5-difluorophenyl) | CN |
| (147) | n-Propyl | — | —CH$_2$—CH$_2$— | (2,3-difluorophenyl) | OCF$_3$ |
| (148) | n-Propyl | — | —CH$_2$—CH$_2$— | (phenyl) | O-n-Propyl |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A cyclohexane compound of formula I

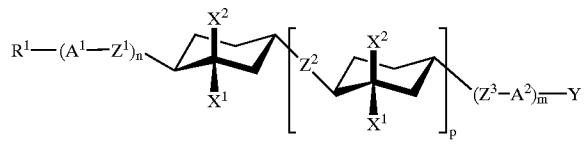

wherien
Y is alkyl or alkoxy having 1 to 10 carbon atoms which is optionally at least monosubstituted by halogen, is alkenyl or alkenyloxy having 2 to 10 carbon atoms which is optionally at least monosubstituted by —CN, —CF$_3$ or —F, or is —CN, —F, —OCHF$_2$, —OCF$_3$, —OCHFCF$_3$ or —OCF$_2$CF$_3$, one of X$^1$ and X$^2$ is CF$_3$, CHF$_2$, CH$_2$F, OCHF$_2$, OCF$_3$, SF$_5$ or an alkyl radical having 2 to 10 carbon atoms which is monosubstituted or polysubstituted by fluorine or chlorine, and one of X$^1$ or X$^2$ in each cyclohexane ring is H, R$^1$ is H, alkyl or alkenyl having 1 to 12 carbon atoms which is optionally monosubstituted by CN or CF$_3$ or at least monosubstituted by halogen, where one or more non-adjacent CH$_2$ groups is optionally independently replaced by

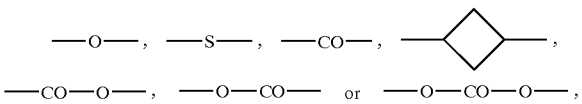

A$^1$ and A$^2$, are each independently
 a) a trans-1,4-cyclohexylene radical, in which at least one or more non-adjacent CH$_2$ group is optionally independently replaced by —O— or —S—,
 b) a 1,4-phenylene radical, in which, one or two CH groups is optionally replaced by N,
 c) 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, or
 d) 1,4-cyclohexenylene,
wherein a), b) and d) is optionally substituted by CN, Cl or F, Z$^1$, Z$^2$ are each independently, —CO—O—, and Z$^3$ —O—CO—, CH$_2$O—, —O—, —O—CH$_2$—, —CH$_2$CH$_2$—, —CH=CH—, —C≡C—, —CF$_2$CF$_2$——CF$_2$O—, —OCF$_2$— or a single bond, n and m, are each independently 0, 1, 2 or 3, and p is 0, 1, 2 or 3, where m+n+p is 1, 2, 3 or 4.

2. A cyclohexane compound of formula I according to claim 1, wherein n is 0or 1, and m and p are 0, 1 or 2.

3. A cyclohexane compound of formula I according to claim 1, wherein Z$^1$, Z$^2$ and Z$^3$, are each independently —CH$_2$CH$_2$—, —CH=CH— or a single bond.

4. A cyclohexane compound of formula I according to claim 1, wherein R$^1$ is straight-chain alkyl or alkoxy having 1 to 10 carbon atoms or alkenyl having 2 to 10 carbon atoms, and Y is alkyl having 1 to 10 carbon atoms, alkenyl having 2 to 10 carbon atoms, —CN, —F, —OCHF$_2$ or —OCF$_3$.

5. A cyclohexane compound of formula I according to claim 1, wherein R and Y are each alkyl having 1 to 10 carbon atoms, and n is 0 and m is 1.

6. A cyclohexane compound according to claim 1, wherein X$^1$ or X$^2$ is CF$_3$.

7. A liquid-crystalline medium having at least two liquid-crystalline components, comprising at least one compound of the formula I according to claim 1.

8. A liquid-crystal display element, comprising a liquid-crystalline medium according to claim 7.

9. An electro-optical display element, comprising a dielectric, a liquid-crystalline medium according to claim 7.

10. A liquid-crystal medium comprising a chiral dopant, wherein the chiral dopant is a compound according to claim 1.

* * * * *

UNITED STATES PATENT AND TRADEMARK OFFICE
CERTIFICATE OF CORRECTION

PATENT NO. : 6,551,666 B2
DATED : April 22, 2003
INVENTOR(S) : Peer Kirsch et al.

It is certified that error appears in the above-identified patent and that said Letters Patent is hereby corrected as shown below:

Title page,
Item [73], Assignee, reads "Mit," should read -- Mit Beschraenketer Haftung, --

Column 49,
Line 37, reads "Z1, Z2 are each" should read -- Z1, Z2 and Z3 are each --

Column 50,
Line 1, reads "and Z3-O-CO-," should read -- -O-CO-, --
Line 3, reads "-CF2CF2-CF2O-," should read -- -CF2CF2-, -CF20-, --
Line 11, reads "is 0or 1," should read -- is 0 or 1, --
Line 22, reads "R and Y" should read -- R1 and Y --

Signed and Sealed this

Thirty-first Day of August, 2004

JON W. DUDAS
*Director of the United States Patent and Trademark Office*